(12) United States Patent
Westbye et al.

(10) Patent No.: US 9,339,031 B2
(45) Date of Patent: May 17, 2016

(54) HYDROPHOBICALLY MODIFIED POLYSACCHARIDE ETHERS AS DEPOSITION ENHANCERS FOR AGRICULTURAL ACTIVE INGREDIENTS

(75) Inventors: Peter Westbye, Stenungsund (SE); Leif Olof Karlson, Stenungsund (SE)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 167 days.

(21) Appl. No.: 13/994,396

(22) PCT Filed: Dec. 13, 2011

(86) PCT No.: PCT/EP2011/072500
§ 371 (c)(1),
(2), (4) Date: Jun. 14, 2013

(87) PCT Pub. No.: WO2012/080196
PCT Pub. Date: Jun. 21, 2012

(65) Prior Publication Data
US 2013/0274110 A1    Oct. 17, 2013

Related U.S. Application Data

(60) Provisional application No. 61/423,726, filed on Dec. 16, 2010.

(30) Foreign Application Priority Data

Dec. 16, 2010 (EP) .................................. 10195409

(51) Int. Cl.
*A01N 25/24* (2006.01)
*A01N 25/30* (2006.01)

(52) U.S. Cl.
CPC ............... *A01N 25/24* (2013.01); *A01N 25/30* (2013.01)

(58) Field of Classification Search
CPC ..... A01N 39/04; A01N 43/653; A01N 25/24; A01N 25/30
USPC ................... 514/383, 781; 504/358
See application file for complete search history.

(56) References Cited

U.S. PATENT DOCUMENTS

| | | | |
|---|---|---|---|
| 5,747,416 A * | 5/1998 | McArdle | 504/115 |
| 5,776,479 A | 7/1998 | Pallos et al. | |
| 6,320,043 B1 * | 11/2001 | Weber et al. | 536/84 |
| 6,433,061 B1 | 8/2002 | Marchant et al. | |
| 6,534,563 B1 | 3/2003 | Bergeron et al. | |
| 6,645,476 B1 | 11/2003 | Morschhäuser et al. | |
| 2002/0111480 A1 * | 8/2002 | Weber et al. | 536/123.1 |
| 2002/0177526 A1 | 11/2002 | Chen et al. | |
| 2004/0214736 A1 * | 10/2004 | Modi | 510/238 |
| 2004/0258764 A1 | 12/2004 | Murphy et al. | |
| 2005/0053569 A1 | 3/2005 | Bavouzet et al. | |
| 2006/0134047 A1 * | 6/2006 | Bakeev et al. | 424/70.13 |
| 2006/0193789 A1 * | 8/2006 | Tamarkin | A61K 8/046 424/47 |
| 2007/0149409 A1 | 6/2007 | Burnet et al. | |
| 2009/0298695 A1 | 12/2009 | Wu et al. | |

FOREIGN PATENT DOCUMENTS

| | | |
|---|---|---|
| FR | 2727830 | 6/1996 |
| WO | WO92/03048 A1 | 3/1992 |
| WO | WO92/09197 A1 | 6/1992 |
| WO | WO97/39626 A1 | 10/1997 |
| WO | WO98/56825 A1 | 12/1998 |
| WO | WO99/31211 A1 | 6/1999 |
| WO | WO 9931211 A1 * | 6/1999 |
| WO | 00/08058 A1 | 2/2000 |
| WO | WO00/71591 A1 | 11/2000 |
| WO | WO2006/065848 A1 | 6/2006 |
| WO | 2007/145709 A1 | 12/2007 |

OTHER PUBLICATIONS

English Abstract of FR2727830.
Derycke V et al, Effect of Adjuvants on the Activity of Fungicides in Winter Wheat Under Field Conditions, Med. Fac. Landbouww. Univ. Gent, 63/6b, 1998, pp. 1041-1045.
International Patent Application Search Report of PCT/EP2011/072500, mailed Aug. 10, 2012.

* cited by examiner

*Primary Examiner* — Janet Epps-Smith
*Assistant Examiner* — Courtney Brown
(74) *Attorney, Agent, or Firm* — Matthew D. Kellam

(57) ABSTRACT

A composition is provided, comprising a non-ionic, water-soluble, hydrophobically modified lower alkyl hydroxyalkyl linear polysaccharide ether, wherein the hydrophobic group comprises a long-chain C10-C18 alkyl or alkenyl group, the lower alkyl group has 1-4 carbon atoms, and the hydroxyalkyl groups are hydroxyethyl and/or hydroxypropyl; and one or more agriculturally active ingredient. A method for treating a plant is also provided, comprising the step of contacting a plant with a composition of the invention.

17 Claims, No Drawings

HYDROPHOBICALLY MODIFIED POLYSACCHARIDE ETHERS AS DEPOSITION ENHANCERS FOR AGRICULTURAL ACTIVE INGREDIENTS

This application is a National Stage entry of International Application PCT/EP2011/072500, filed Dec. 13, 2011, which claims the benefit of U.S. Patent Application No. 61/423,726, filed Dec. 16, 2010, and European Patent Application No, 10195409.7, filed Dec. 16, 2010. The contents of the aforementioned applications are incorporated herein by reference in their entireties.

FIELD OF INVENTION

The present invention relates to the use of certain water-soluble, hydrophobically modified linear polysaccharide ethers, in particular cellulose ether derivatives, as deposition enhancers for agriculturally active ingredients in aqueous solutions. It further relates to compositions comprising said cellulose ether derivatives and at least one agriculturally active ingredient, the use of said compositions for treatment of plants and to methods for treating a plant by contacting the plant with a composition of the invention.

BACKGROUND OF THE INVENTION

Agriculturally active ingredients, such as pesticides and plant growth regulators are conventionally distributed by spraying. There is however a problem for agrochemical spray droplets, mostly consisting of water, to deposit onto waxy plant leaf surfaces. One plausible reason for this is that the kinetic energy that the droplets have been given due to atomization when sprayed, is transformed into surface energy upon impact with the leaf surface. The droplet stretches out on the surface, but this high surface tension is not favourable, which means that the droplet is pulled back. This pullback is so energetic that part of the droplet, or even the complete droplet, detaches from the leaf surface. According to literature, as much as 90% of the solution sprayed onto the leaf could be lost by this phenomenon. There are two known ways to solve this problem, namely by adding a surfactant that can quickly go to the surface and lower the surface tension, or by adding a polymer to control the cohesion of the droplet. However, using a surfactant gives rise to another problem, namely the problem of drift. Both the problem with pullback and that with drift will reduce bio efficacy, since the agriculturally ingredient(s) will not reach the plant. By using polymers the problem with drift can be avoided. There are a number of different publications relating to polymers in pesticidal compositions for different purposes.

WO 98/56825 relates to a hydrophobically modified anionic cellulose ether used in anti-settling, associative thickening, and in foam, emulsion, and suspension stabilizations, in a number of different industries, e.g. in a time-released application including pesticides.

U.S. Pat. No. 6,534,563 B1 relates to the use of compounds with particular elongational and flow viscosity as an anti-rebound agent included in aqueous plant protection formulations. The compounds used are selected from hydrosoluble or hydrodispersible surfactant polymers with a molecular weight in the range $5\times10^5$ to $5\times10^6$ g/mol, including polysaccharide derivatives, such as cellulose and its carboxyalkylated or hydroxyalkylated derivatives, wherein the alkyl portion contains 1 to 4 carbon atoms.

WO 92/09197 relates to a herbicidal preparation comprising a polymeric stabiliser selected from a group of polymers all of which have a molecular weight of at least 7,000 Dalton, including hydrophobically modified non-ionic cellulose ethers.

However, there is still a need in the art for compositions comprising agriculturally active ingredients, which compositions have improved deposition properties.

SUMMARY OF THE INVENTION

One object of the present invention is to provide alternative polymers as deposition enhancers for agriculturally active ingredients, usually pesticides and/or plant growth regulators.

Another object of the invention is to provide compositions, preferably aqueous compositions, comprising the polymer and one or more agriculturally active ingredient.

The inventors have now surprisingly found that a non-ionic, water-soluble, hydrophobically modified lower alkyl hydroxyalkyl linear polysaccharide ether, in particular a cellulose ether, wherein the hydrophobic group, with which the polysaccharide ether is hydrophobically modified, comprises a long-chain C10-C18, preferably C12-C16, and most preferably C12-C14, alkyl or alkenyl group, preferably having a $MS_{hydrophobe}$ of 0.001-0.02; the lower alkyl group has 1-4 carbon atoms, preferably 1-2 carbon atoms, said group preferably having a $DS_{alkyl}$ of 0.1-2.5, more preferably 0.2-2.0, and most preferably 0.3-1.5; and the hydroxyalkyl groups are hydroxyethyl and/or hydroxypropyl preferably having a $MS_{hydroxyalkyl}$ of 0.2-4.0, exhibits excellent properties as a deposition enhancer for agriculturally active ingredients.

DETAILED DESCRIPTION OF THE INVENTION

As mentioned above, a non-ionic, water-soluble, hydrophobically modified alkyl hydroxyalkyl linear polysaccharide ether, in particular a cellulose ether, wherein the hydrophobic group, with which the polysaccharide ether is hydrophobically modified, comprises a long-chain C10-C18, preferably C12-C16, and most preferably C12-C14, alkyl or alkenyl group, preferably having a $MS_{hydrophobe}$ of 0.001-0.02; the lower alkyl group has 1-4 carbon atoms, preferably 1-2 carbon atoms, said group preferably having a $DS_{alkyl}$ of 0.1-2.5, more preferably 0.2-2.0, and most preferably 0.3-1.5; and the hydroxyalkyl groups are hydroxyethyl and/or hydroxypropyl preferably having a $MS_{hydroxyalkyl}$ of 0.2-4.0; exhibits excellent properties as a deposition enhancer for agriculturally active ingredients.

The terms $DS_{alkyl}$, $MS_{hydrophobe}$, and $MS_{hydroxyalkyl}$ are used in their regular connotation, and give an overall account of the average number of the different substituents per anhydroglucose unit. DS, the degree of substitution, is the average number of hydroxyl positions on the anhydroglucose unit that have been reacted, and can by definition vary between 0 and a maximum of 3. MS, the molar substitution, is defined as the number of moles of reagent present per mole of anhydroglucose unit. This number could by definition be higher than 3. For example, once a hydroxyl group of the anhydroglucose unit has reacted with one reagent molecule, e.g. with an alkylene oxide molecule, the newly formed hydroxyl group can further react with an additional alkylene oxide molecule. The process could then be repeated several times, forming polyoxyalkylene chains.

The degree of substitution of hydroxyalkyl and alkyl groups, $MS_{hydroxyalkyl}$ and $DS_{alkyl}$, can be determined by gas chromatography following degradation of the cellulose ether with HBr in glacial acetic acid, according to the procedure set out in Stead, J. B., & Hindley, H., (1969) "A modified method for the analysis oxyethylene/oxypropylene copolymers by chemical fission and gas chromatography" Journal of Chromatography, 42, 470-475.

More particularly, as understood by the above definitions, the linear polysaccharide ether contains the above-mentioned groups as ether substituents on the anhydroglucose units. The lower alkyl substituents are methyl, ethyl, propyl or butyl, or combinations thereof. The $DS_{alkyl}$, which refers to the lower alkyl groups having 1-4 carbon atoms, is adapted to the hydrophobicity of these alkyl groups, which means that DS is normally lower for the more hydrophobic groups propyl and butyl than it is for methyl and ethyl. $DS_{methyl}$ is suitably 0.3-2.5, preferably 0.5-2.0, and most preferably 0.7-1.9. $DS_{ethyl}$ is suitably 0.1-1.5, preferably 0.3-1.2, and most preferably 0.5-1.0.

The hydroxyalkyl substituents are hydroxyethyl and/or hydroxypropyl, and optionally the linear polysaccharide ether, in particular cellulose ether, may further contain smaller amounts of hydroxybutyl substituents. The substituents and the degree of substitution are chosen so that the associative linear polysaccharide ethers, in particular cellulose ethers, of the invention become water-soluble.

Herein a product will be defined as water soluble, if after adding 1 g of product per liter water (0.1% by weight) with stirring at 25° C., adjustment of the pH to a value of 6-7, using NaOH or HCl as appropriate, and after further stirring for 16 hours at said temperature, at least 20, preferably at least 40, more preferably at least 60, even more preferably at least 80 and most preferably at least 90% by weight of the product added is dissolved in the water. The $MS_{hydroxyalkyl}$ of the linear polysaccharide ether of the present invention may vary within wide limits but is normally within a range of 0.2-4.0, suitably 1.0-3.0, and preferably 1.5-2.8. The $MS_{hydroxyethyl}$ is also normally within this general range. The $MS_{hydroxypropy}$ is normally within a range of 0.1-2.0, suitably 0.2-1.7, and preferably 0.3-1.5. If hydroxybutyl groups are present, the $MS_{hydroxybutyl}$ is normally <0.5.

The longer hydrophobic groups are suitably derived from a glycidyl ether or a chloroglyceryl ether of a C10 to C18, preferably C12 to C16, and most preferably C12 to C14 alcohol that is preferably ethoxylated; from a C10 to C18, preferably C12 to C16, and most preferably C12 to C14 alkyl halide; or from a C12 to C20, preferably C14 to C18, and most preferably C14 to C16 α-olefin epoxide. The product typically has a $MS_{hydrophobe}$ of 0.001 or more, preferably 0.003 or more, and most preferably 0.005 or more. The $MS_{hydrophobe}$ is preferably 0.020 or less, more preferably 0.015 or less, and most preferably 0.010 or less.

The linear polysaccharide ethers, in particular cellulose ethers, of the invention may be prepared by using known process steps (described e.g. in "Cellulose ethers" by T. G. Majewicz and T. J. Podlas in *Kirk Othmer Encyclopedia of Chemical Technology*, Vol. 5, pp. 445-466, online posting date: Dec. 4, 2000). For example, alkali cellulose and suitable reactants can be reacted in the presence of an alkaline catalyst in order to introduce lower alkyl groups and hydroxyalkyl groups in such amounts that the intermediate cellulose ethers obtained are water-soluble. This intermediate cellulose ether product and a hydrophobic reactant having the formula

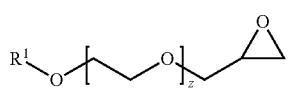

(I)

or the formula

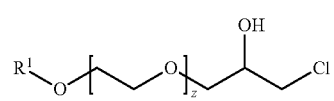

(II)

in which $R^1$ is an alkyl or alkenyl group with 10-18, preferably 12-16, and most preferably 12-14 carbon atoms and z is a number between 0-10, preferably 1-5; or a reactant having the formula $R^1X$ (III), where X is a halide atom, are then reacted at an elevated temperature and in the presence of an alkaline catalyst to form a cellulose ether according to the invention.

In another embodiment the hydrophobic reactant has the formula

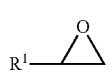

(IV)

in which $R^1$ is an alkyl or alkenyl group with 10-18, preferably 12-16, and most preferably 12-14 carbon atoms.

The hydrophobic reagents (I) and (II) are most preferred.

The order of the different steps of the process is not critical and can be any order. For example, the reagent used for hydrophobic modification may be added to an intermediate hydroxyethyl cellulose ether comprising an alkyl group with 1-4 carbon atoms, the alkyl group usually having a $DS_{alkyl}$ of 0.1-2.5. The intermediate cellulose ether is made by adding ethylene oxide, optionally together with propylene oxide and/or butylene oxide, and an alkyl halide, such as methyl, ethyl, propyl or butyl chloride, to alkali cellulose. If this route is followed, the intermediate cellulose ether that is used as starting material preferably has a cloud point of below 100° C. and most preferably from 25° C. to 85° C. More preferred is a route where the reagent used for hydrophobic modification, usually a lower alkyl halide, and ethylene oxide are added to alkali cellulose, followed by a stepwise rising of the temperature. As described above, the cellulose ether is hydrophobically modified, for example by reacting the cellulose ether with an epoxide of formula (I) or a chloroglyceryl ether of formula (II) obtained from a fatty alcohol or an ethoxylated fatty alcohol via the epichlorohydrin route; from a long-chain alkyl halide of formula (III); or from an α-olefin epoxide of formula (IV).

Suitable water-soluble nonionic cellulose derivatives that may be used as starting materials for the hydrophobically modified cellulose derivatives of the present invention are methyl hydroxyethyl cellulose, methyl hydroxypropyl cellulose, ethyl hydroxyethyl cellulose, propyl hydroxyethyl cellulose, butyl hydroxyethyl cellulose, methyl ethyl hydroxyethyl cellulose, and methyl hydroxyethyl hydroxypropyl cellulose. Preferred cellulose ethers are methyl hydroxyethyl cellulose, methyl ethyl hydroxyethyl cellulose, methyl hydroxypropyl cellulose, and ethyl hydroxyethyl cellulose.

Suitable examples of long-chain alkylating reagents are hydrophobic epoxides or halides containing an alkyl or alkenyl group with 10 to 16 carbon atoms, such as dodecanol+ 2EO-glycidyl ether, tetradecanol+4EO-glycidyl ether, dodecyl bromide, and tetradecyl bromide. The hydrophobic alkylating agent can also be a mixture of compounds having different chain lengths.

The cellulose ethers of the invention are polymers that may be represented by the structural formula

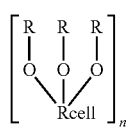 (V)

where $R_{cell}$ is the residue of an anhydroglucose unit ($C_6H_{10}O_5$), and the separate R-groups may be the same or different and each R individually represents a substituent group of the formula (VI) given below, and n represents the degree of polymerisation (DP) and is usually an integer having a value of from about 500 to about 10,000.

In the above structural formula (V), for the embodiment where the hydrophobic reactant (I) or (II) has been used in the preparation of the product, each R individually may be represented by a substituent group of the general formula

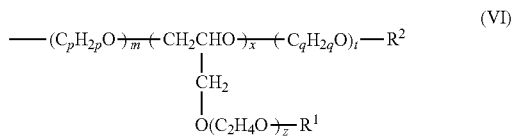 (VI)

where p and q independently are 2, 3 or 4, preferably 2, m is a number between 0-5, x is a number between 0-2, t is a number between 0-5, z is a number between 0-10, $R^1$ is an alkyl or alkenyl group with 10-18 carbon atoms, preferably 12-16 carbon atoms, and most preferably 12-14 carbon atoms, and $R^2$ is an alkyl group with 1-4 carbon atoms or hydrogen. However, the cellulose ether as a whole should always comprise substituents where p and/or q are 2 or 3, where x is 1-2, and where m and/or t are >0.

Thus, one specific hydroxyl group of the cellulose may react with one or several of the reagents. For example, the hydroxyl group could first react with one or several ethylene oxide molecules, then there could be a further reaction with a compound of formula (I), followed by reaction with a C1-C4 alkyl halide. Another possibility would be a direct reaction with just one of the reactants mentioned above, or with any combination of two of them. When there has been a reaction with a C1-C4 alkyl halide, no further substituents can be added to that position, since there will be no more hydroxyl group available to react with in that case.

As is shown in the formula (V) above, each anhydroglucose unit of the cellulose ether has a maximum of three positions that may be substituted, and the substituents R may be represented by the general formula (VI). The substituents for each specific anhydroglucose unit in the same cellulose molecule will obviously more or less differ from one another, and the formulae (V) and (VI) cannot by themselves adequately describe the polymer. The $DS_{alkyl}$, $MS_{hydrophobe}$, and $MS_{hydroxyalkyl}$ are normally used for this purpose, since these will give an overall account of the average number of the different substituents per anhydroglucose unit.

A composition of the invention comprises at least one agriculturally active ingredient, usually a pesticide and/or a plant growth regulator. The agriculturally active ingredient is usually an organic, more usually synthetic, compound or mixture of such compounds.

As used herein, the term "pesticide" refers to an organic compound which will prevent, destroy, repel or mitigate any pest. Pesticides contemplated for use in the present invention include fungicides, herbicides, insecticides, miticides, nematicides, acaricides, and molluscicides.

As used herein, the term "plant growth regulator" refers to an organic compound, which through physiological action will accelerate or retard the rate of growth or rate of maturation or otherwise alter the behaviour of ornamental or crop plants or the products thereof. Plant growth regulators contemplated for use in the present invention include abscisic acids, auxins, cytokinins and gibberellins.

Preferred pesticides contemplated for use in the present invention include pesticides and plant growth regulators of the classes triazoles, strobilurins, alkylenebis(dithiocarbamate) compounds, benzimidazoles, phenoxy carboxylic acids, benzoic acids, sulfonylureas, triazines, pyridine carboxylic acids, neonicotinides, amidines, organophosphates, and pyrethroids, and salts and esters of the acid compounds.

Examples of fungicides contemplated for use in the present invention include fungicides of the classes triazoles (e.g. tebuconazole, tetraconazole, cyproconazole, epoxiconazole, difenconazole, propiconazole, prothioconazole), strobilurins (e.g. trifloxystrobin, azoxystrobin, fluoxastrobin, pyraclostrobin), alkylenebis(dithiocarbamate) compounds (e.g. mancozeb) and benzimidazoles (e.g carbendazim).

Examples of herbicides contemplated for use in the present invention include phenoxy carboxylic acids (e.g. 2,4-D-acid, MCPA), benzoic acids (e.g. Dicamba-acid), sulfonylureas (e.g. methylsulfuron-methyl, rimsulfuron), triazines (e.g. atrazine and simazine), triazolinones (e.g. amicarbazone) and pyridine carboxylic acids (e.g. triclopyr).

Examples of insecticides contemplated for use in the present invention include neonicotinides (e.g. thiamethoxam, clothianidin, thiacloprid, dinotefuran, acetamiprid, nitenpyram, imidacloprid), amidines (e.g. amitraz), organophosphates (e.g. chlorpyrifos) and pyrethroids (e.g. permethrin, bifenthrin, deltamethrin).

For a detailed description of each of the above-mentioned pesticides and plant growth regulators, reference is made to handbooks, e.g. "The e-Pesticide Manual v4.0" from BCPC Publications Ltd, Alton, Hampshire. (ISBN 1 901396 42 8).

In addition to the hydrophobically modified hydroxyethyl alkyl cellulose ether and the agriculturally active ingredient(s), the compositions of the invention may contain additional components. Non-limiting examples of such additional components include for example oils, co-solvents, and other adjuvants, such as surfactants, that are conventionally used to increase the bioefficacy of agricultural active ingredients.

A composition according to the invention may be a so called "ready-to-use" composition, in which the polysaccharide ether and the agriculturally active ingredients are formulated in an aqueous medium to their intended end-use concentrations, i.e. the concentrations at which the composition is to be used.

Such a ready-to-use composition usually comprises at least 0.005, preferably at least 0.01, more preferably at least 0.02, still more preferably at least 0.03, and most preferably at least 0.04% (w/w) of the polysaccharide ether according to the invention, and at most 0.5, preferably at most 0.4, more preferably at most 0.3, even more preferably at most 0.2, still more preferably at most 0.18, still more preferably at most 0.15, and most preferably at most 0.1% (w/w) of the polysaccharide ether according to the invention; and at least 0.005, preferably at least 0.01, more preferably at least 0.02, and most preferably at least 0.03% (w/w) of the at least one agriculturally active ingredient, and at most 2, preferably at most 1, more preferably at most 0.5, and most preferably at most 0.4% (w/w) of the at least one agriculturally active ingredient.

A composition according to the invention may be a concentrated composition, a "pre-use" composition, in which the polysaccharide ether and the agriculturally active ingredient are formulated at a concentration higher than the intended end-use, optionally in a solvent different from water. Such a pre-use composition should preferably be diluted with an aqueous medium, usually water, before its end-use.

The polysaccharide ether and the agriculturally active ingredient may also be available as separate articles, to be sold separate or together as a kit, which are to be mixed together to form an aqueous end-use formulation of the invention.

The present invention further provides for a method for treating a plant, wherein the plant is contacted with a composition of the invention. The desired amount of agriculturally active ingredient to be contacted with a plant by means of such method depends on several parameters, such as the biological activity of the agriculturally active ingredient, but generally, the amount is adjusted to be sufficient for the agriculturally active ingredient to perform its desired activity.

As used herein, "plant" includes all parts of a plant, including roots, stems, leaves, flowers and fruits.

In one embodiment of the treatment method, any part of the plant, such as a leaf, flower, fruit and/or stem of is contacted with a formulation of the present invention by means of spraying.

In a further aspect, the present invention relates to the use of a non-ionic, water-soluble, hydrophobically modified lower alkyl hydroxyalkyl linear polysaccharide ether as defined herein in connection to the composition of the invention, as a deposition enhancer for aqueous compositions comprising at least one agriculturally active ingredient.

In yet a further aspect, the present invention relates to a method for improving the deposition on a plant of an aqueous composition comprising at least one agriculturally active ingredient, the improvement comprising adding to the composition a non-ionic, water-soluble, hydrophobically modified lower alkyl hydroxyalkyl linear polysaccharide ether as defined herein in connection to the composition of the invention.

With the exception of the information in the examples, or where otherwise indicated, all numbers or expressions referring to quantities of ingredients, reaction conditions, and the like used in the specification and claims are to be understood as modified in all instances by the term "about". Further, where numerical ranges are disclosed, they are meant to be continuous ranges that include every value between the minimum and maximum value as presented. Wt % and % w/w mean percent by weight.

The invention will now be further described in connection with the following Examples, which, however, are not intended to limit the scope thereof. Unless otherwise stated, all parts and percentages refer to parts and percentages by weight. All numbers given relate to the amount of active material. So if in the examples 10% w/w of a chemical is specified, then the amount to be used of the supplied product is to be increased if the product is supplied in a diluted form.

The present invention will now be illustrated by the following non-limiting examples.

GENERAL EXPERIMENTAL

In Table 1 the structural data for the investigated polymers are collected.

TABLE 1

| Product | Hydrophobe | $MS_{hydroxyethyl}$ | $DS_{ethyl}$ | $DS_{CM}$ | $DS_{BGE}$ | $MS_{hydrophobe}$ |
|---|---|---|---|---|---|---|
| EHEC | no hydrophobe | 2.1 | 0.8 | 0 | 0 | 0 |
| HM(NP)-EHEC[a] | nonyl phenol | 2.1 | 0.8 | 0 | 0 | 0.008 |
| HM(C14)-EHEC[b] | tetradecanol | 2.1 | 0.8 | 0 | 0 | 0.008 |
| HM(C14)-CMC[b] | tetradecanol | 0 | 0 | 0.8 | 0.16 | 0.007 |

[a]The hydrophobic reagent used for preparation was a glycidyl ether similar to formula (I) where z = 1.1, but where $R^1$ is nonyl phenol
[b]The hydrophobic reagent used for preparation was a glycidyl ether having formula (I) where z = 2 and $R^1$ is tetradecyl.

The substitution degrees of ethylene oxide ($MS_{hydroxyethyl}$), ethyl ($DS_{ethyl}$), carboxymethyl ($DS_{CM}$), a butyl glycidylether ($DS_{BGE}$), and hydrophobic tails ($MS_{hydrophobe}$) of each of the polymer samples are given as average numbers of substituents per repeating glucose unit. The abbreviations given in the "Hydrophobe" column refer to the unmodified parent EHEC (no hydrophobe), HM-EHEC modified with nonylphenol groups (NP) and with C14 groups (C14), and carboxymethyl cellulose modified with C14 groups (C14). The molecular substitution, MS, of the hydrophobic groups was determined by the method described by Landoll, L. M., *J Polym. Sci. Part A: Polymer Chem.*, 1982, 20, 443-455.

Since the DP viscosity is independent of hydrophobic interactions in the solution, the DP viscosity can be used to compare DP (degree of polymerisation) for different cellulose ethers, both hydrophobically modified and non-hydrophobically modified (see U.S. Pat. No. 6,362,238 B2 and EP 1 694 711 B1). The DP viscosity can be measured using a conventional rheometer, such as a TA instruments AR-G2, using a 40 mm, 1° cone and plate measurement system, at a shear stress of 0.5 Pa and a temperature of 20° C. The DP viscosity, as used throughout this document, is determined by dissolving the polymer in a solvent system consisting of 20% by weight of di(ethylene glycol) monobutyl ether and 80% by weight of water at 20° C. The viscosities obtained are then divided by a factor 2.7, in order to compensate for the higher viscosities obtained in an aqueous solution containing 20% by weight of di(ethylene glycol) monobutyl ether in comparison with the viscosities obtained in pure water.

TABLE 2

| Product | DP viscosity (m Pa s) |
|---|---|
| EHEC | 15 |
| HM(NP)-EHEC | 40 |
| HM(C14)-EHEC | 23 |
| HM(C14)-CMC | 18 |
| Natrosol 330C Plus | 16 |

As is shown in Table 2, all the products that have been evaluated as deposition enhancers in the experiments below exhibit DP viscosities within the same order of magnitude, and thus have comparable molecular weights. Natrosol 330C Plus is a cetyl ether of hydroxyethyl cellulose (HM-HEC) available from Aqualon.

EXAMPLE 1

Evaluation of Polymers as Deposition Enhancers

The polymers indicated in Table 2 above was been tested for their performance as deposition enhancers by the following method:

A syringe is placed 0.5 m above a flat surface. The height corresponds to a droplet velocity through the relationship; potential energy in syringe equals kinetic energy at the surface ($mgh=mv^2/2$), where m is the mass, v the velocity, g the gravity constant, and h the height. $v=(2\,gh)^{1/2}$ gives a velocity of 3.1 m/s with a height of 0.5 m with the assumption that there is no friction from the air. The droplets have a mean diameter of 2,800 μm as determined by weighing 100 droplets and calculating the dimensions with the density of water. The flat surface which the droplets are landing on is covered with a layer of Parafilm (Pechiney Plastic Packaging Company), which mimics the hydrophobic leaf surface. The slope of this surface may be changed. The steeper the slope, the tougher it gets for the droplets to adhere to the surface. The slopes are reported in degrees, where 0 degrees means a horizontal surface and 90 degrees means a vertical surface.

A total of five droplets are allowed to collide with the surface at every fifth degree; if at least 3 of the droplets adhere (deposit) immediately (i.e. without sliding or scattering), the liquid is considered to adhere at that angle. The slope is increased by five degrees until 3 out of five droplets do not adhere to the surface.

The results are presented in Tables 3-6 for the polymer concentrations of 0.2%, 0.1%, 0.04%, and 0.02% (w/w), respectively. In the Tables deposition is designated by D and runoff by R. With pure water (no polymer present) at least 3 of 5 droplets deposit at an angle of 15° and run off at an angle of 20°.

TABLE 3

Deposition study of droplets at 0.2% concentration of polymers.

| | Polymer | | | | |
|---|---|---|---|---|---|
| Angle (°) | Natrosol 330C Plus) Comparison | HM(C14)-CMC Comparison | HM(NP)-EHEC Comparison | EHEC Comparison | HM(C14)-EHEC |
| 0 | D | D | D | D | D |
| 5 | D | D | D | D | D |
| 10 | D | D | D | D | D |
| 15 | D | D | D | D | D |
| 20 | D | D | D | D | D |
| 25 | D | D | D | D | D |
| 30 | D | D | D | D | D |
| 35 | D | R | D | D | D |
| 40 | D | R | D | D | D |
| 45 | D | R | D | D | D |
| 50 | R | R | D | D | D |
| 55 | R | R | R | R | D |
| 60 | R | R | R | R | D |
| 65 | R | R | R | R | R |

TABLE 4

Deposition study of droplets at 0.1% concentration of polymers.

| | Polymer | | | | |
|---|---|---|---|---|---|
| Angle (°) | Natrosol 330C Plus Comparison | HM(C14)-CMC Comparison | HM(NP)-EHEC Comparison | EHEC Comparison | HM(C14)-EHEC |
| 0 | D | D | D | D | D |
| 5 | D | D | D | D | D |
| 10 | D | D | D | D | D |
| 15 | D | D | D | D | D |
| 20 | D | D | D | D | D |
| 25 | D | D | D | D | D |
| 30 | D | R | D | D | D |
| 35 | D | R | D | D | D |
| 40 | D | R | D | D | D |
| 45 | R | R | D | D | D |
| 50 | R | R | D | D | D |
| 55 | R | R | R | R | D |
| 60 | R | R | R | R | R |
| 65 | R | R | R | R | R |

TABLE 5

Deposition study of droplets at 0.04% concentration of polymers.

| | Polymer | | | | |
|---|---|---|---|---|---|
| Angle (°) | Natrosol 330C Plus Comparison | HM(C14)-CMC Comparison | HM(NP)-EHEC Comparison | EHEC Comparison | HM(C14)-EHEC |
| 0 | D | D | D | D | D |
| 5 | D | D | D | D | D |
| 10 | D | D | D | D | D |
| 15 | D | D | D | D | D |
| 20 | D | D | D | D | D |
| 25 | D | D | D | D | D |
| 30 | R | R | D | D | D |
| 35 | R | R | D | D | D |
| 40 | R | R | D | D | D |
| 45 | R | R | R | R | D |
| 50 | R | R | R | R | D |
| 55 | R | R | R | R | R |
| 60 | R | R | R | R | R |
| 65 | R | R | R | R | R |

TABLE 6

Deposition study of droplets at 0.02% concentration of polymers.

| | Polymer | | | | |
|---|---|---|---|---|---|
| Angle (°) | Natrosol 330C Plus Comparison | HM(C14)-CMC Comparison | HM(NP)-EHEC Comparison | EHEC Comparison | HM(C14)-EHEC |
| 0 | D | D | D | D | D |
| 5 | D | D | D | D | D |
| 10 | D | D | D | D | D |
| 15 | D | D | D | D | D |
| 20 | D | D | D | D | D |
| 25 | D | D | D | D | D |
| 30 | R | R | D | D | D |
| 35 | R | R | D | R | D |
| 40 | R | R | R | R | D |
| 45 | R | R | R | R | D |
| 50 | R | R | R | R | R |
| 55 | R | R | R | R | R |
| 60 | R | R | R | R | R |
| 65 | R | R | R | R | R |

From the experimental results collected in the Tables 3-6 above it is evident that non-ionic cellulose ethers are better than anionic cellulose ethers in terms of deposition properties. It is also concluded that cellulose ether derivatives containing both ethyl and hydroxyethyl substituents (EHEC) possess better deposition properties than cellulose ether derivatives containing only hydroxyethyl substituents (HEC). Further, it is concluded that hydrophobically modified EHECs possess better deposition properties than non-hydrophobically modified EHEC if the hydrophobic group is an alkyl group, but only marginally so if the hydrophobic group is a nonyl phenol group.

EXAMPLE 2

Deposition Angle of Agricultural Formulations

The HM(C14)-EHEC was suspended in deionized water to a concentration of 0.2% w/w and thereafter swelled by the addition of ammonia to a pH above 8 and continuously stirred for an hour. Another sample of deionized water was saturated with an agriculturally active ingredient, and the pH of was adjusted to 7 and more agriculturally active ingredient was added until saturation. The agricultural active solution was filtered for solids and the solution was mixed in a ratio of 1:1 with the 0.2% HM(C14)-EHEC solution. The ready to use sample (0.1% w/w HM(C14)-EHEC, 50% of the saturation level of active ingredient) was tested for the deposition angle according to the description in Example 1 above part.

The results are listed in table 7:

TABLE 7

Deposition angles for compositions comprising agricultural actives

| Active ingredient | Water solubility (mg/l)* | Deposition at (°) |
|---|---|---|
| Metconazole | 30.4 | 55 |
| 2,4-D acid | 45000 | 55 |

*e-Pesticide Manual v 4.0 (BCPC Publications, ISBN 1 901396 42 8)

For both Metconazole and 2,4-D acid as the agriculturally active ingredient, compositions of the invention deposited on the surface at an angle of 55° C.

The invention claimed is:

1. A composition comprising from 0.005 to 0.4% (w/w) of a non-ionic, water-soluble, hydrophobically modified lower alkyl hydroxyalkyl linear polysaccharide ether, wherein the hydrophobic group comprises a long-chain C10-C18 alkyl or alkenyl group, the lower alkyl group has 1-4 carbon atoms, and the hydroxyalkyl groups are hydroxyethyl and/or hydroxypropyl; and from 0.005 to 0.5% (w/w) of one or more agriculturally active ingredients.

2. A composition according to claim 1, wherein said agriculturally active ingredient is selected from the group consisting of pesticides and plant growth regulators.

3. A composition according to claim 1, comprising at least one pesticide selected from the group consisting of fungicides, herbicides, insecticides, miticides, nematicides, acaricides, and molluscicides.

4. A composition according to claim 1, comprising at least one pesticide selected from the group consisting of triazoles, strobilurins, benzimidazoles, phenoxy carboxylic acids, benzoic acids, sulfonylureas, pyridine carboxylic acids, neonicotinides, amidines, and pyrethroids, and salts and esters of the acid compounds.

5. A composition according to claim 1, comprising at least one plant growth regulator selected from the group consisting of abscisic acids, auxins, cytokinins and gibberellins.

6. A composition according to, wherein the linear polysaccharide ether is a cellulose ether having a $MS_{hydrophobe}$ of 0.001-0.02.

7. A composition according to claim 1 wherein said hydrophobic group comprises a long-chain C12-C14 alkyl or alkenyl group.

8. A composition according to claim 1, wherein the linear polysaccharide ether has a $DS_{alkyl}$ of 0.1-2.5 for the lower alkyl group.

9. A composition according to claim 1, wherein the linear polysaccharide ether has a $MS_{hydroxyalkyl}$ of 0.2-4.0.

10. A composition according to claim 1, wherein the linear polysaccharide ether is a cellulose ether having a $MS_{hydroxyethyl}$ of 0.2-4.0.

11. A composition according to claim 1, wherein the linear polysaccharide ether is a cellulose ether having a $MS_{hydroxypropyl}$ of 0.1-2.0.

12. A composition according to claim 1 wherein the substituents of the non-ionic, water-soluble, hydrophobically modified lower alkyl hydroxyalkyl linear polysaccharide ether have the general formula 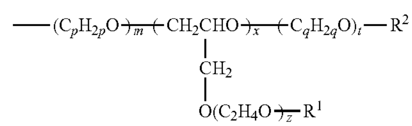 (VI)

where p and q independently are 2, 3 or 4, m is a number between 0-5, x is a number between 0-2, t is a number between 0-5, z is a number between 0-10, $R^1$ is an alkyl or alkenyl group with 10-18 carbon atoms, and $R^2$ is an alkyl group with 1-4 carbon atoms or hydrogen, provided the cellulose ether molecule as a whole always comprises substituents where p and/or q are 2 or 3, where x is 1-2, and where m or t is >0.

13. A composition according to claim 12, wherein $R^1$ is an alkyl group with 12-14 carbon atoms.

14. A method for the treatment of a plant comprising the step of contacting the plant with an aqueous composition comprising a non-ionic, water-soluble, hydrophobically modified lower alkyl hydroxyalkyl linear polysaccharide ether, wherein the hydrophobic group comprises a long-chain C10-C18 alkyl or alkenyl group, the lower alkyl group has 1-4 carbon atoms, and the hydroxyalkyl groups are hydroxyethyl and/or hydroxypropyl; and one or more agriculturally active ingredient.

15. A method according to claim 14 where the composition is sprayed onto the leaves of the plant.

16. A method for improving the deposition on a plant of an aqueous composition comprising from 0.005 to 0.5% (w/w) of at least one agriculturally active ingredient, said method comprising the step of adding to said composition from 0.005 to 0.4% (w/w) of a non-ionic, water-soluble, hydrophobically modified lower alkyl hydroxyalkyl linear polysaccharide ether, wherein the hydrophobic group comprises a long-chain C10-C18 alkyl or alkenyl group, the lower alkyl group has 1-4 carbon atoms, and the hydroxyalkyl groups are hydroxyethyl and/or hydroxypropyl.

17. A method according to claim 14, wherein the aqueous composition comprises from 0.005 to 0.4% (w/w) of the polysaccharide ether and from 0.005% to 0.5% (w/w) of the agriculturally active ingredient.

* * * * *